(12) United States Patent
Miguez et al.

(10) Patent No.: US 8,216,821 B2
(45) Date of Patent: Jul. 10, 2012

(54) REGULATION OF HETEROLOGOUS RECOMBINANT PROTEIN EXPRESSION IN METHYLOTROPHIC AND METHANOTROPHIC BACTERIA

(75) Inventors: Carlos B. Miguez, Beaconsfield (CA); Young-Jun Choi, Pierrefonds (CA); Alaka Mullick, Montreal (CA); Bernard Massie, Laval (CA)

(73) Assignee: National Research Council of Canada, Ottawa, Ontario (CA)

( * ) Notice: Subject to any disclaimer, the term of this patent is extended or adjusted under 35 U.S.C. 154(b) by 683 days.

(21) Appl. No.: 11/990,779

(22) PCT Filed: Aug. 21, 2006

(86) PCT No.: PCT/CA2006/001371
§ 371 (c)(1),
(2), (4) Date: Feb. 21, 2008

(87) PCT Pub. No.: WO2007/022623
PCT Pub. Date: Mar. 1, 2007

(65) Prior Publication Data
US 2010/0221813 A1    Sep. 2, 2010

Related U.S. Application Data

(60) Provisional application No. 60/710,158, filed on Aug. 23, 2005.

(51) Int. Cl.
C12N 1/21 (2006.01)
C12N 15/74 (2006.01)
(52) U.S. Cl. .............. 435/252.34; 435/252.3; 435/320.1
(58) Field of Classification Search .................... None
See application file for complete search history.

(56) References Cited

U.S. PATENT DOCUMENTS

| | | | |
|---|---|---|---|
| 5,302,525 A | | 4/1994 | Groleau et al. |
| 5,356,796 A | * | 10/1994 | Keller .......................... 435/69.1 |
| 5,972,708 A | * | 10/1999 | Sherratt et al. ................ 435/479 |
| 6,743,780 B1 | * | 6/2004 | Hanak et al. ................ 514/44 R |
| 7,026,464 B2 | * | 4/2006 | Dicosimo et al. ............ 536/23.1 |
| 7,670,824 B2 | * | 3/2010 | Miguez et al. ............. 435/252.3 |
| 7,745,592 B2 | * | 6/2010 | Massie et al. ................ 536/23.1 |

(Continued)

FOREIGN PATENT DOCUMENTS

CA 2446110 11/2002

(Continued)

OTHER PUBLICATIONS

Weber, W et al, Current Opinion in Biotechnology, Aug. 5, 2004 (online publication), vol. 15, pp. 383-391, Approaches for trigger-inducible viral transgene regulation in gene-based tissue engineering.*

(Continued)

Primary Examiner — Albert Navarro
Assistant Examiner — Ginny Portner
(74) Attorney, Agent, or Firm — Johanna Coutts; Cassan Maclean

(57) ABSTRACT

Methylotrophic or methanotrophic bacteria such as *Methylobacterium* are transformed with a gene of interest, and expression of the gene is regulated by means of a cumate repressor protein and an operator sequence which is operatively linked to the gene of interest, and the addition of an external agent. Specifically, the cymR repressor and cmt operator from *Pseudomonas putida* may serve to regulate gene expression in methylotrophic or methanotrophic bacteria with the addition of cumate.

12 Claims, 7 Drawing Sheets

U.S. PATENT DOCUMENTS

| | | | |
|---|---|---|---|
| 7,935,788 B2* | 5/2011 | Malenfant et al. | 530/350 |
| 2002/0143142 A1* | 10/2002 | Lin et al. | 530/324 |
| 2003/0157636 A1* | 8/2003 | Figueira et al. | 435/69.1 |
| 2004/0205834 A1* | 10/2004 | Massie et al. | 800/13 |
| 2005/0249701 A1* | 11/2005 | Morre et al. | 424/85.2 |
| 2006/0234336 A1 | 10/2006 | Miguez et al. | |
| 2007/0104732 A1* | 5/2007 | Massie et al. | 424/204.1 |
| 2008/0026005 A1 | 1/2008 | Miguez et al. | |
| 2008/0300618 A1* | 12/2008 | Gertner | 606/192 |
| 2008/0311618 A1* | 12/2008 | Xu et al. | 435/69.1 |
| 2009/0176275 A1* | 7/2009 | Malenfant et al. | 435/69.1 |

FOREIGN PATENT DOCUMENTS

| | | | |
|---|---|---|---|
| CA | 2553485 | | 1/2007 |
| WO | WO 02088346 A2 | | 7/2002 |
| WO | 2004/018681 | * | 3/2004 |
| WO | 02/088346 | * | 2/2007 |

OTHER PUBLICATIONS

Kalyaeva, M.A. et al, 2003 The effect of aerobic methylotrophic bacteria on the in vitro morphogenesis of Soft Wheat, Russian Journal of Plant Physiol. 50:313-317.

Romanovskaya, V.A.et al, 2001 The ways of plant colonozation by *Methylobacterium* strains and properties of these bacteria. Microbiology 70, 221-227.

Chistoserdova, L. et al, 2003 Methylotrophy in *Methylobacterium extorquens* AM1 from a genomic point of view. J. Bacteriol. 185: 2980-2987.

Belanger, L. et al 2004 Production of heterologous protein by *Methylobacterium extorquens* in high cell density fermentation FEMS Microbiol.Lett. 231: 197-204.

Fitzgerald, K.A. and M.E. Lidstrom 2003 Overexpression of a heterologous protein, haloalkane dehalogenas, in a poly-B-hydroxybutyrate.. AM1 Biotechnol.Bioeng. 81: 263-268.

Figueira, M.M. et al 2000 Production of green fluoroescent protein by the methylotrophic bacterium . . . FEMS Microbiol. Lett. 193: 195-200.

Marx, C.J. et al 2003, Novel methylotrophy genes of *Methylobacterium extorquens* AM1 identified by using transposon . . . J Bacteriol. 185: 669-73.

Marx, C.J. et al 2004 Development of an insertional expression vector system for *Methylobacterium extorquens*.. Microbiology 150: 9-19.

Anthony, C. 1993 Methanol dehydrogenase in Gram-negative bacteria In: Davidson V(ed) Principles & Applns of quinoproteins, Dekker NY, pp. 17-45.

Davidson, V.L. 1993 Methylamine dehydrogenase In:Davidson V(ed) Principles and applications of quinoproteins, Dekker, NY, pp. 73-85.

Trotsenko, Y.A. et al 2001 Aerobic methylotrophic bacteria as phytosymbionts. Microbiology 70: 623-632.

Bourque,D.B. et al 1992 Production of poly-B-hydroxybutyrate from methanol: characterization of a new isolate.. Applied Microbiology & Biotech. 37:7-12.

Bourque,D.Y. et al 1995 High cell density production of poly-beta-hydroxybutyrate (PHB) Appl.Microbiol. Biotechnol.44:367-376.

Van Dien,S.J. et al 2003 Genetic characterization of the carotenoid biosynthetic pathway . . . Appl Environ Microbiol. 69:7563-6.

Doronina,N.V. et al 2002 New evidence for the ability of methylobacteria and methanotrophs to synthesize auxins. Microbiology 71: 116-118.

Lidstrom, M.E. & L. Chistoserdova 2002 Plans in the pink: Cytokinin production by *Methylobacterium*. J. Bacteriol. 184: 1818.

Choi, Y.J. et al 2004 Characterization and heterologous gene expression of a novel esterase from *Lactobacillus casei* CL96 Appln Environ. Microbiol. 70: 3213-3221.

Gutierrez, J.D. et al 2005, Heterologous extracellular production of enterocin P from *Enterococcus faecium* P13 . . . FEMS Microbiol. Lett. 248: 125-131.

Zhang M. & M.E. Lidstrom 2003, Promoters and transcripts for genes involved in methanol oxidation . . . Am1 Microbiol. 149: 1033-1040.

Eaton, R.W. 1996 p-Cumate catabolic pathway in *Pseudomonas putida* F1: cloning & characterization of DNA carrying . . . J. Bacteriol. 178: 1351-1362.

Eaton, R.W. 1997 p-Cymene catabolic pathway in *Pseudomonas putida* F1: cloning and characterization of DNA encoding . . . J. Bacteriol. 179: 3171-3180.

Koch,B. et al 2001 A panel of Tn7-based vectors for insertion of the gfp marker gene or for delivery of cloned DNA . . . J. Microbiol. Methods 45: 187-195.

Choi,Y.J. et al 2006 Multicopy-integration of heterologous genes and expression in the methylotroph *Methylobacterium* . . . ATCC 55366. Appl.Environ Microbiol.72: 753-759.

Marx, C.J. & M.E. Lidstrom 2001 Development of improved versatile broad-host-range vectors for use in methylotrophs . . . Microbiology, 147: 2065-2075.

Hung,M.N. et al 2001 Molecular and Biochemical Analysis of Two B-Galactosidases from *Bifidobacterium infantis* HL96 Appln Environ Microbiol. 67: 4256-4263.

Kademi, A. et al 1999 Effect of culture condition on growth and esterase production by the moderate thermophile . . . MAS2. J. Ind. Mirobiol. Biotech 23: 188-193.

Sambrook, J. & D.W. Russel 1989, Molecular Cloning (2nd ed.), Cold Spring Harbor Laboratory, Cold Spring Harbor, NY.

Bradford, M.M. 1976 A rapid and sensitive method for the quantitation of microgram quantities of protein utilizing the principle of protein . . . Anal. Biochem. 72: 248-254.

Marx C.J. and Lidstrom M.E. Development of improved versatile broad-host-range vectors for use in methylotrophs and other Gram-negative bacteria. Microbiology. Aug. 2001, vol. 147, pp. 2065-2075, ISSN: 1350-0872.

Belanger L. et al. Production of heterologous protein by *Methylobacterium extorquens* in high cell density fermentation. FEMS Microbiology Letters. Feb. 2004, vol. 231, No. 2, pp. 197-204, ISSN: 0378-1097.

Eaton R. W. p-Cymene catabolic pathway in *Pseudomonas putida* F1: Cloning and characterization of DNA encoding conversion of p-Cymene to p-Cumate. J. Bacteriology May 1997, vol. 179, No. 10, pp. 3171-3180, ISSN: 0021-9193.

* cited by examiner

REGULATION OF HETEROLOGOUS RECOMBINANT PROTEIN EXPRESSION IN METHYLOTROPHIC AND METHANOTROPHIC BACTERIA

RELATED APPLICATIONS

This is a national stage entry application claiming the benefit of PCT Application No. PCT/CA2006/001371, which claims priority to U.S. Provisional Application Ser. No. 60/710,158, filed Aug. 23, 2005.

FIELD OF THE INVENTION

The invention relates to the regulation of gene expression in transformant methylotrophic or methanotrophic cells by means of a repressor-operator system.

BACKGROUND OF THE INVENTION

Methylotrophic bacteria are ubiquitous, inhabiting different aquatic and terrestrial habitats including the phyllosphere. In addition to their important role in the cycling of single carbon compounds in the environment, methanol-utilizing methylotrophs have been shown to enter into plant-growth-promoting phytosymbiotic relationships (1, 2). Amongst the methylotrophs, several *Methylobacterium* species have been well described in the literature. One of the best characterized strains within the *Methylobacterium* genus, both genetically and physiologically, is the methanol utilizing *Methylobacterium extorquens* AM1 (3). Another well characterized *M. extorquens* strain, ATCC 55366, was isolated for its capacity to produce high quantities of poly-β-hydroxybutyric acid. A fed-batch fermentation system was developed specifically for this strain to further enhance its growth potential and PHB productivity. See also U.S. Pat. No. 5,302,525, which issued Nov. 23, 1992.

*Methylobacterium extorquens* has received special attention as a potential source of industrially pertinent natural and recombinant proteins (4, 5). The industrial potential of *M. extorquens* as a producer of recombinant proteins is due to: (i) the simplicity of its growth requirements and a comparably inexpensive substrate (methanol); (ii) the development and optimization of protocols for high cell density cultivation; (iii) the sequencing and annotation of the *M. extorquens* AM1 genome; and (iv) the development of genetic tools specifically for *M. extorquens* comprising novel cloning and expression vectors, efficient transposon mutagenesis, integrative expression vectors and protocols, and simple and efficient electroporation protocols (6-8). The potential of *M. extorquens* and other pink pigmented facultative methylotrophs (PPFMs) as "cell factories" is further enhanced by their inherent capabilities to produce natural products of great import including pyrroloquinoline quinone (9, 10), vitamin B12 (11), poly-β-hydroxybutyric acid (12, 13), caratenoids (14), and phytohormones (15, 16). By applying the molecular tools and high cell-density fermentation technologies mentioned above, it has been possible to overexpress a variety of recombinant proteins in *M. extorquens* strains ATCC 55366 and AM1. Representative proteins overexpressed in these two *M. extorquens* strains include the green fluorescent protein, esterase from *Lactobacillus casei*, enterocin P from *Enterococcus faecium*, and haloalkane dehalogenase from *Xanthobacter autotrophicus* (4, 17, 18, 19). Several of these activities are the subject of our pending U.S. patent application Ser. No. 10/497,060, filed Nov. 29, 2002. Miguez et al.

However, as it concerns *Methylobacterium extorquens* strains AM1 and ATCC 55366, practical and tight inducible expression of recombinant genes has not been attained (20). Inducible heterologous promoters have been tested in *M. extorquens* ATCC 55366, in particular $P_{lac}$ and $\lambda P_L$ and $P_R$ (Choi et al., unpublished results) however expression is both leaky and weak. *M. extorquens* possesses native methanol inducible promoters, notably promoters which are located upstream of genes that encode for the methanol dehydrogenase and other proteins required for its activity, and for enzymes required for the synthesis of the methanol dehydrogenase prosthetic group, the pyrroloquinoline quinone. Of these, promoter $P_{mxaF}$ has been thoroughly scrutinized both biochemically and in expression studies. Although it is a very strong promoter (4, 17, 20), in practical terms it is essentially constitutive. Expression of the green fluorescent gene (gfp) under the control of $P_{mxaF}$ occurred even when the culture was grown repeatedly on succinate.

SUMMARY OF THE INVENTION

A first object of the invention is to provide a method for regulating the production of recombinant proteins in methylotrophic or methanotrophic bacteria such as *Methylobacterium*. This may be done by means of a repressor-operator system that is operatively linked to a gene of interest.

A further object of the invention is to provide a method for regulating heterologous gene expression in *Methylobacterium extorquens*.

A first aspect of the invention provides for a polynucleotide construct for use in association with a methylotrophic or methanotrophic host cell, the host cell comprising a nucleotide that encodes a cumate repressor protein exhibiting repressor activity which is regulatable by the addition of an external agent, and the polynucleotide construct comprising a promoter fused to an operator sequence which is operatively linked to at least one gene of interest, wherein the operator sequence is in operative association with the cumate repressor protein and wherein addition of the external agent upregulates expression of the at least one gene of interest.

A second aspect of the invention provides for a methylotrophic or methanotrophic host cell comprising a nucleotide that encodes a cumate repressor protein exhibiting repressor activity which is regulatable by the addition of an external agent, and further comprising a polynucleotide construct which comprises a promoter fused to an operator sequence which is operatively linked to at least one gene of interest, wherein the operator sequence is in operative association with the cumate repressor protein and wherein addition of the external agent upregulates expression of the at least one gene of interest.

A third aspect of the invention provides for a gene expression system comprising a methylotrophic or methanotrophic host cell comprising a nucleotide that encodes a p-cumate repressor protein exhibiting repressor activity which is regulatable by the addition of an external agent, and further comprising a polynucleotide construct which comprises a promoter fused to an operator sequence which is operatively linked to at least one gene of interest, wherein the operator sequence is in operative association with the cumate repressor protein and wherein addition of the external agent upregulates expression of the at least one gene of interest.

A further aspect of the invention provides for a method for selectively controlling the expression of at least one gene of interest comprising the steps of a) obtaining a methylotrophic or methanotrophic host cell comprising a nucleotide that encodes a cumate repressor protein exhibiting repressor activity which is regulatable by the addition of an external agent, and further comprising a polynucleotide construct which comprises a promoter fused to an operator sequence which is operatively linked to at least one gene of interest, wherein the operator sequence is in operative association with the cumate repressor protein and wherein expression of the at least one gene of interest is repressed due to the repressor activity of the repressor protein; and b) exposing the host cell to an external agent which inhibits the repressor activity and allows for expression of the at least one gene of interest.

DETAILED DESCRIPTION OF THE INVENTION

Figure 1:
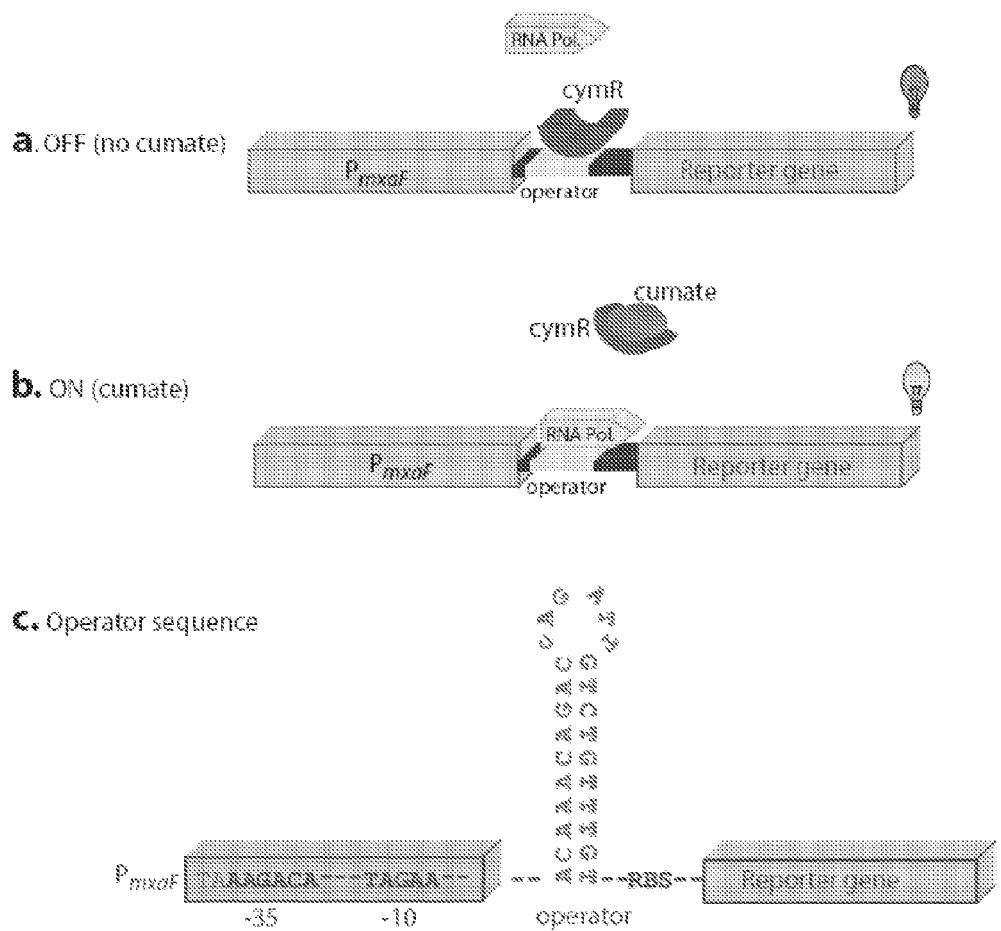
FIG. 1. A schematic diagram of the mechanism of action of the cumate-switchable expression system. (a) In the absence of the inducer, cumate, the repressor protein (cymR) is bound to the operator site upstream of the reporter gene or gene of interest, and inhibits transcription. (b) The presence of the cumate is necessary for transcription of gene of interest. The addition of cumate rapidly alters the binding of the operator to the repressor cymR, thereby facilitating the formation of the cymR-cumate complex. The detachment of the cymR from the operator activates transcription of the downstream reporter gene. The cymR-cumate complex is unable to bind to operator site. (c) Nucleotide sequence of the operator (SEQ ID NO: 19), which represents the putative binding site for the helix-turn-helix transcription factor.

The invention disclosed relates to the development of a methylotrophic or methanotrophic host cell recombinant protein expression system. More specifically, the methylotrophic or methanotrophic host cell may be of the genus *Methylobacterium*, and even more specifically may be of the species *Methylobacterium extorquens*. It is desirable to be able to control the production of a recombinant protein, as constitutive production of the protein may not be desirable. Such control may be achieved using a repressor-operator regulation system such as the regulatory elements of the *Pseudomonas putida* F1, namely the cym and cmt operons, enabling inducible/regulated gene expression.

First, the gene encoding for a repressor protein, such as cymR, is integrated into the chromosome of the methylotrophic or methanotrophic host cell downstream of a strong native promoter. Second, an expression vector is constructed by inserting a strong native constitutive promoter, such as $P_{mxaF}$ or other suitable promoter such as λ, and the repressor protein binding sites or operator region downstream of the transcription start site for a gene of interest, such as a reporter gene. This vector is then transferred by electroporation to the host cell containing the chromosomally integrated repressor protein gene. Addition of an external agent or inducer to the culture prevents the binding of the repressor to the operator region thereby alleviating transcription repression and resulting in the tight inducible expression of the reporter gene. While the experimental data discussed herein relates to *Methylobacterium extorquens* host cells, it is expected that the method should work in other *Methylobacterium* strains as well as other methylotrophic bacteria, due to the high degree of genetic similarity between the strains. Further, the use of the strong native promoter $P_{mxaF}$ produced good results, and it is known that the $P_{mxaF}$ promoter in other methylotrophic and methanotrophic bacteria has high homology to that of *M. extorquens*. Accordingly, it is expected that other methanotrophic and methylotrophic host cells will be suitable for the methods described herein.

While other repressor/operator systems may be effective, in this case the regulatory elements of the *P. putida* F1 cym and cmt operons have been adapted, thus enabling inducible/regulated gene expression.

The metabolism of p-cymene (p-isopropyltoluene) by *P. putida* F1 is tightly regulated (21, 22). *P. putida* F1 degrades p-cymene (p-isopropyltoluene) through p-cumate (p-isopropylbenzoate) to isobutyrate, pyruvate, and acetyl coenzyme A. The genes encoding the enzymes required for this degradation are grouped in two distinct operons. The cym operon encodes the conversion of p-cymene to p-cumate, and located downstream of the cym operon is the cmt operon which encodes the catabolism of p-cumate. A regulatory protein known as cymR, encoded upstream of the cym operon, has been shown to bind to specific operator-promoter regions in both operons and controls expression of both operons. Induction is afforded by p-cumate, the end product of the first operon, but not by p-cymene. Accordingly, the cymR gene and the operator fragment of the cmt operon were chosen for the construction of the inducible expression system for *M. extorquens*.

The construction strategy of the system is as follows. First, two copies of the gene encoding for the repressor protein cymR are integrated into the chromosome of *M. extorquens* under the control of the strong native $P_{mxaF}$ promoter. This promoter is, in practical terms, constitutive in *M. extorquens*. This recombinant repressor-expressing strain, *M. extorquens* (cymR2), is the host strain for subsequent plasmid transformations. Chromosomal integration of the cymR genes was achieved using the mini-Tn7 transposon system technology recently described in our Provisional (U.S.) patent application, No. 60/702,291, filed Jul. 26, 2005.

Second, an expression vector (pCUM-gene of interest) is constructed containing the strong native $P_{mxaF}$ promoter, followed by the cymR binding site (operator sequence), and followed by the gene of interest to be expressed. This expression vector is then cloned in the *M. extorquens* (cymR2). In the absence of the inducer, cumate, gene expression is repressed. Addition of cumate to the culture reduces the binding capacity of the repressor protein (cymR) to the operator region. Transcription repression is thereby alleviated and tight inducible expression of the reporter gene is attained.

The basic mechanism of this system is summarized in FIG. 1. To test cumate-inducibility, we expressed the green fluorescent protein (GFP) and two other selected proteins (esterase, estI and β-galactosidase, bgl) in the recombinant host strain *M. extorquens* (cymR2).

The development of an inducible/regulated gene expression system is an important addition to the *M. extorquens*' expression "tool box". Possible applications include the commercial expression of recombinant proteins, including that of toxic or difficult-to-express proteins. This new tool permits modulated expression capability which may become useful when attempting to express potentially difficult or toxic proteins to the host. This tool may also be very useful in metabolic flux studies and methanolic pathway engineering.

Materials and Methods

Bacterial strains and growth conditions The bacterial strains and plasmids used in this invention are listed in Table 1.

TABLE 1

Strains and plasmids used in this study

| Strain or plasmid | Description | Reference or source |
|---|---|---|
| *M. extorquens* strains | | |
| ATCC 55366 | Wild-type | ATCC |
| CymR1 | Modified host strain containing single copy of cymR expression casstte in the chromosome | This study |
| CymR2 | Modified host strain containing double copy of cymR expression casstte in the chromosome | This study |
| GFP | *M. extorquens* CymR2 containing pCUM-gfp | This study |
| BGL | *M. extorquens* CymR2 containing pCUM-bgl | This study |
| EST | *M. extorquens* CymR2 containing pCUM-est | This study |
| *Pseudomonas putida* F1 | Source of cymR gene in the cym operon | 22 |
| *E. coli* strains | | |
| Top10 | Strain for cloning and propagating plasmid DNA | Invitrogen Inc. |
| S-17/λ pir | Host strain for pUX-BF13 | 23 |
| Plasmids | | |
| pBK-miniTn7-ΩSm2 | pUC19-based delivery plasmid for a miniTn7-Km transposon; Km$^r$, Sm$^r$ | 24 |
| pBRI-tet | pUC19-based delivery plasmid for a miniTn7 transposon; Tet$^r$ | This study |
| pBRI80 | pUC19-based delivery plasmid for a miniTn7 transposon containing $P_{mxaF}$ and RBS; Tet$^r$ | This study |
| pBRI-cymR1 | pBRI80 plasmid containing one copy of cymR expression cassette | This study |
| pBRI-cymR2 | pBRI80 plasmid containing two copies of cymR expression cassettes | This study |
| pUX-BF13 | R6K replicon based helper plasmid | 23 |
| pCR2.1-TOPO | PCR cloning vector | Invitrogen Inc. |
| pCR-cymR | pCR2.1-TOPO plasmid containing cymR | This study |
| PCR-MDHOP | pCR2.1-TOPO plasmid containing $P_{mxaF}$-operator | This study |
| pCR-bgl | pCR2.1-TOPO plasmid containing bgl | This study |
| pCR-est | pCR2.1-TOPO plasmid containing estI | This study |
| pCR-gfp | pCR2.1-TOPO plasmid containing gfp | This study |
| pCM110 | Wide-host range cloning vector containing $P_{mxaF}$; Tet$^r$ | 25 |
| pCHOI3 | Wide-host range cloning vector containing $P_{mxaF}$; Km$^r$ | This study |
| pCUM50 | Newly constructed regulative expression vector for *M. extorquens* (cymR+) | This study |
| pCUM-bgl | pCUM50 plasmid containing lactase expression cassette | This study |

TABLE 1-continued

Strains and plasmids used in this study

| Strain or plasmid | Description | Reference or source |
|---|---|---|
| pCUM-est | pCUM50 plasmid containing esterase expression cassette | This study |
| pCUM-gfp | pCUM50 plasmid containing gfp expression cassette | This study |
| pUC19 | Multi-purpose cloning vector | Invitrogen Inc. |
| pCESTa | Esterase gene source | 17 |
| pEBIG4 | Lactase gene source | 26 |
| pQBI63 | GFP gene source | Qbiogene Inc. |

M. extorquens (ATCC 55366) was used for the preparation of the heterologous gene expression host. E. coli strain Top10 was used for cloning and propagation of recombinant DNA and S17-1λpir (recA, thi, pro, hsdR⁻M⁺ RP4:2-Tc:Mu:Km Tn7, pir lysogen; $Sm^R$, $Tp^R$) was used for propagation of the helper plasmid (23). E. coli was cultured in Luria Bertani broth (LB) at 37° C. Strain of M. extorquens was grown in CHOI medium, as previously described (17) and 1% (v/v) methanol was used as sole carbon source. Both media were solidified by 1.8% agar (Difco) when appropriate. Antibiotics were used for E. coli and M. extorquens at the following concentrations (in ug/ml): ampicillin, 100; kanamycin (Km), 40; tetracyclin (Tc), 35.

Construction of expression host strains The expression host M. extorquens (cymR+) Was constructed by insertion of the cymR gene of P. putida F1 using the mini-Tn7 integration system using the mini-Tn7 vector pBRI80 with helper plasmid (23, 24). Primers used in the cymR amplification were designed on the basis of the nucleotide sequence of P. putida F1 cym operon (22). In order to achieve tight regulated induction, two copies of cymR gene were integrated into the M. extorquens chromosome. Briefly, the mini-Tn7 base vector pBRI80 was constructed as follows: a 1,955-bp PstI fragment containing TetA and TetR was amplified from pCM110 (25) by PCR using primers Tet-F-Pst (5'-GCTGCAGTCAATCGTCACCCTTTCTCGGTC-3' (SEQ ID NO: 1)) (PstI site is underlined) and Tet-R-Pst (5'-GCTGCAGTCAGCGATCGGCTCGTTGCCCTG-3' (SEQ ID NO: 2)) (PstI site is underlined). This fragment was then replaced with a kanamycin resistant gene in the pBK-miniTn7-ΩSm2 to form pBRI-tet.

The $P_{mxaF}$-RBS was amplified from pCESTc using primers MDH-F-PstI (5'-GGCTGCAGGTTGACGACAACGGTGCGATG-3' (SEQ ID NO: 3)) (PstI site is underlined) and MDH-R-MluI (5'-CCGACGCGTATGTATATCTCCTTCTTAAAG-3' (SEQ ID NO: 4)) (MluI site is underlined). The PCR fragment containing $P_{mxaF}$-RBS was cloned into pBRI-tet which was partially digested with PstI/MluI to delete $Sm^R/Sp^R$ cassette, to generate pBRI80.

To generate pBRI-cymR1, cymR was amplified from chromosomal DNA of P. putida F1 Using primers CYM-F-Afl (5'-GCTTAAGAAGATGGTGATCATGAGT CCAAAGAGAAGAAC-3' (SEQ ID NO: 5)) (AflII site is underlined) and CYM-R-Not (5'-CAGCGGCCGCCTAGCGCTTGAATTCG CGTAC-CGCTCTCGCG-3'(SEQ ID NO: 6)) (NotI site is underlined). A 612-bp AflII-NotI fragment from pCR-cymR was ligated into the AflII-NotI site of pBRI80 to form pBRI-cymR1. To obtain the pBRI-cymR2 containing two copies of cymR expression cassettes, a second copy of cymR was amplified from pBRI-cymR using primers MDH-CYM-F-Not (5'-CAGCGGCCGCGTTGACGACAAC GGTGC-GATGGGTC-3' (SEQ ID NO: 7)) (NotI site is underlined) and CYM-R-Apa (5'-CAGGGCCCCTAGCGCTTGAATTT CGCGTACCGCTCTCGCG-3' (SEQ ID NO: 8)) (ApaI site is underlined). Amplified fragment containing PmxaF-RBS-cymR was then ligated into the NotI-ApaI site of pBRI-cymR1 to generate pBRI-cymR2.

The genotypes of the cymR-integrated host strains were confirmed by Southern Hybridization using the 612-bp cymR fragment as a probe. Since we have identified the specific Tn7 insertion site (attTn7) in M. extorquens in a previous study (23), the integration of target gene in the chromosome of M. extorquens was also determined by colony PCR using designed primers which include common Tn7 primers ($P_{Tn7R}F$; 5'-ATTAGCTTACGACGCTACACCC-3' (SEQ ID NO: 9) and $P_{Tn7L}R$; 5'-CACAGCA TAACTGG ACT-GATTTC-3' (SEQ ID NO: 10)) and gene specific primers ($P_{dhaT}F$; 5'-CATCGCGATTG TCGATTCGG-3' (SEQ ID NO: 11) and $P_{glmS}R$; 5'-CTGAAGGAAATCAGCTACATC-3' (SEQ ID NO: 12)). The cymR positive strains were finally confirmed by Western blotting. Then, the electro-competent cells were prepared using cymR positive M. extorquens, essentially as described (6, 17).

Inducible expression vector construction. Manipulations and sequencing of DNA were carried out using standard procedures. The operator sequence of cmt operon from P. putida F1 was introduced downstream of the methanol dehydrogenase promoter, $P_{mxaF}$ by polymerase chain reaction. The pCUM50 regulative expression vector was obtained in several steps: first, the PmxaF-synthetic operator sequence was PCR-amplified from pCM110 using primers MDH-F-PST (5'-GCTGCAGGTCGACTCT AGATCA CCTCCT-TAAGC-3' (SEQ ID NO: 13)) (the PstI site is underlined) and MDH-CUM-R (5'-CGAATTCATAATACAAACAGACCAGA TTGTCT-GTTTGTT GCCCTTA GGATCCGCGGTATC-3' (SEQ ID NO: 14)) (the EcoRI site is underlined). The 403 by PCR fragment containing $P_{mxaF}$-operator was cloned into pCR2.1 to create pCR-MDHOP. Next, the kanamycin resistant gene of a 1,218 by PstI fragment from pBK-miniTn7-ΩSm2 was cloned into the PstI site of pCM110, then, tetA and tetR were removed by restriction with BclI and self-ligation yielded pCHOI3. A 403 by PstI-EcoRI fragment from pCR-MDHOP was then ligated between the PstI-EcoRI sites of pCHOI3; this replaced the $P_{mxaF}$ with $P_{mxaF}$-operator to form the pCUM50 cumate inducible expression vector.

To test heterologous protein production using this cumate switch system, we obtained XbaI-ClaI fragment containing gfp gene from pQBI63 and cloned into SpeI-ClaI sites of pCUM50 to generate pCUM-gfp. The 2,100 by fragment carrying the lactase gene (bgl) from Bifidobacterium infantis was amplified from pEBIG4 (26) using primers BGL-F-Nhe (5'-CGCTAGCGAACATAGAGCGTTCAAGTGGC-3' (SEQ ID NO: 15)) (the NheI site is underlined) and BGL-R-

Cla (5'-CATCGATTTACAGCTTGACGACGAGTACGC-CG-3' (SEQ ID NO: 16)) (the ClaI site is underlined). For the amplification of esterase gene (1,800 bp, estI) from *Lactobacillus casei*, pCESTa (17) was used as a template with primers EST-F-Nhe (5'-GGCTAGCGATCAATCTAAAACAAATC-3' (SEQ ID NO: 17)) (the NheI site is underlined) and EST-R-Cla (5'-CATCGATTTATTTATTTGTAATACCGTCTGC-3' (SEQ ID NO: 18)) (the ClaI site is underlined). These NheI-ClaI fragments of bgl and est were then replaced with a gfp gene in the pCUM-gfp to form pCUM-bgl and pCUM-est, respectively. The different proteins tested in the pCUM system were cloned via SpeI and ClaI (GFP) or via Mid and ClaI (BGL and EST).)

Detection of gene expression Detection of GFP was carried out by fluorescence microscopy, and quantified by using a SPECTRAFluor Plus (TECAN Austria Gmbh, GrodIg, Austria) under excitation and emission wavelengths of 485 and 508 nm, respectively. Concentration of GFP was calculated based on a linear relationship between concentration and fluorescence units determined using solutions of purified GFP (Qbiogene). The biomass (X) was determined by cell dry weight measurement of the samples (Moisture Analyzer MA 30, Sartorius).

Esterase activity was determined by a spectrophotometric method using para-nitrophenyl caprylate (pNP-caprylate) as substrate. The rate of hydrolysis of pNP-caprylate at 37° C. was measured in 50 mM sodium phosphate buffer (pH 7.0) according to the method described previously (27). One unit of activity was defined as the amount of enzyme that liberated 1 µmol of p-nitrophenol per min under the given assay conditions. The β-galactosidase activity was measured with o-nitrophenol-β-D-galactoside (ONPG) as a substrate and one unit of activity was defined as the amount of enzyme that liberated 1 µmol of o-nitrophenol per min (28). The protein concentration was estimated by the method of Bradford (29) using the Bio-Rad protein assay kit with bovine serum albumin as a standard.

Western blotting. Integrative expression of repressor protein (cymR) was determined by western blotting using standard protocol. cymR was detected with rabbit anti-bCymR #422 antibody (0.1 g ml$^{-1}$) and a goat anti-rabbit IgG (H+L) HRP conjugate (0.1 µg ml$^{-1}$; Pierce cat#31460, West Grove, Pa.). Cells were lysed in SDS-PAGE sample buffer.

1—Construction of the Inducible Expression System:

1a—Integrative expression of cymR in *M. extorquens*. First, the 612 by cymR gene was cloned under the control of $P_{mxaF}$ promoter, in the chromosome of *M. extorquens* using the Tn7 integration system. Our preliminary experiments showed that *M. extorquens* (cymR1) containing one copy of cymR gene, expressed repressor protein constitutively as expected. However, when the expression vector (pCUM-gfp) described under the heading "Inducible expression vector construction" was used to transform the recombinant host *M. extorquens* (cymR1) culture, only 80% inhibition of reporter gene expression by cymR was achieved (data not shown). It was assumed that this incomplete repression was due to insufficient cymR production. In order to increase the level of cymR expression, a host strain was constructed containing two copies of cymR integrated in the chromosome of *M. extorquens*. This recombinant host, referred as *M. extorquens* (cymR2), showed increased expression of repressor protein. When transformed with pCUM-gfp, GFP expression was almost completely blocked.

Figure 2:
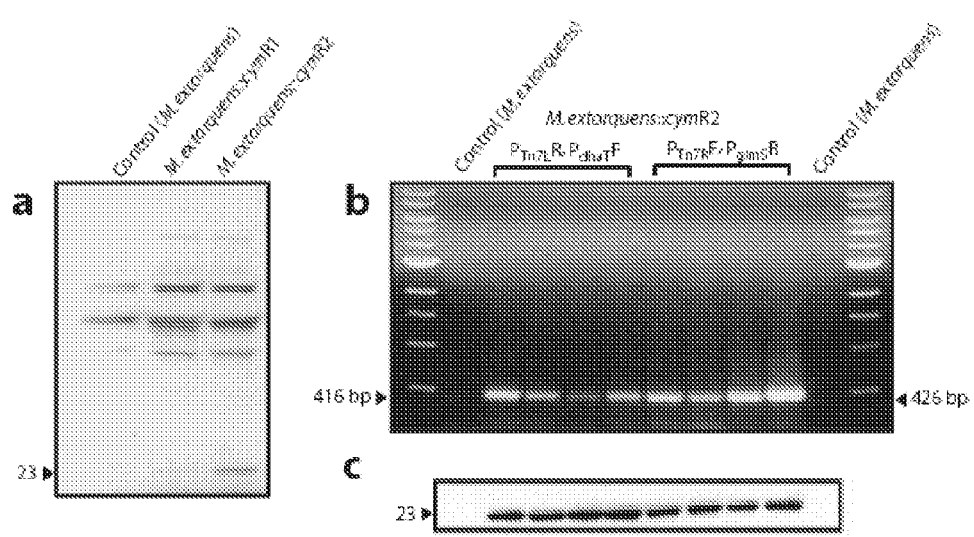
FIG. 2. Analysis of intracellular polypeptides from recombinant strains of M. extorquens::cymR expressing repressor protein. (a) Western blot analysis of repressor protein expressed by native M. extorquens, single copy of cymR integrant and double copy cymR integrant, respectively. Arrows indicate the position and the molecular size (Kda) of the repressor protein. (b) Colony PCR profiles. The physical presence of the integrated cymR gene in the chromosome of M. extorquens was tested in 8 randomly selected clones (cymR2) by colony PCR utilizing the primers described in the experimental protocols. The position and the size of the expected PCR products are marked. $P_{Tn7L}R$, $P_{dhaT}F$, $P_{Tn7R}F$ and $P_{glmS}R$ represent the primers used to generate PCR products. (c) The presence of the repressor protein in 8 randomly selected clones (see b) was confirmed by Western blot analysis.
Figure 3:
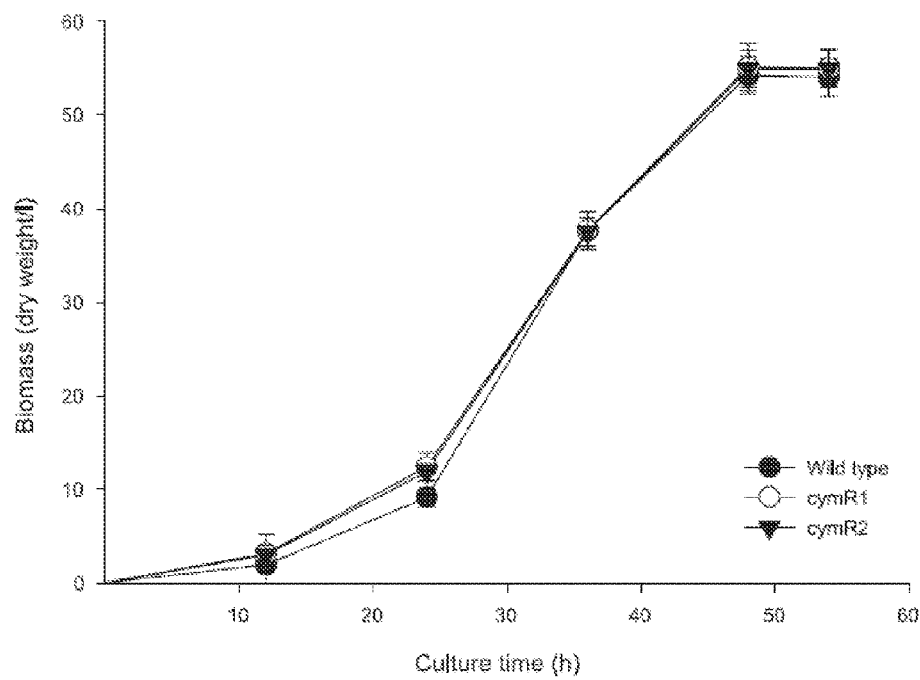
FIG. 3. Comparison of growth profiles between native M. extorquens and modified M. extorquens expressing cymR. Chromosomal integration and expression of cymR using the Tn7 system does not appear to negatively affect the growth and metabolism of M. extorquens. The growth profiles of the native or recombinant strains are indistinguishable, indicating that the repressor protein is not toxic to the host, and the modified recombinant host strain can be used as a new host strain for cumate-inducible expression system.

Insertion of the mini-Tn7-$P_{mxaF}$-cymR into the unique Tn7 attachment site of *M. extorquens* was verified by colony PCR and confirmed by western blotting (FIG. 2). The resulting strain, *M. extorquens* (cymR2), was used as a host strain for the expression plasmids. In this experiment, the amount of biomass generated from modified *M. extorquens* hosts (cymR1, cymR2) at the end of a batch fermentations (~48 h) was almost identical to the native strain (~55 g dry mass per liter), which indicates that cymR gene integration and dosage does not negatively affect the fermentation capability of *M. extorquens*. (FIG. 3).

Figure 4:
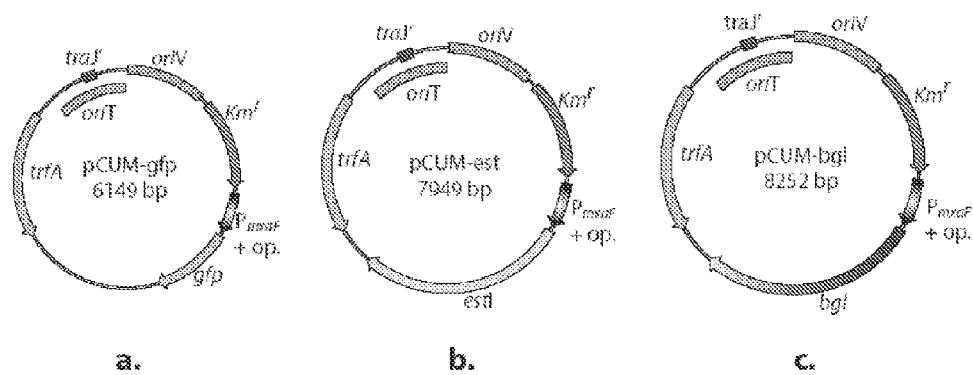
FIG. 4. The maps of recombinant plasmids containing the required regulatory elements. Abbreviations: traJ', mutated conjugal transfer gene that is missing the final 85 of 123 amino acids; oriT, origin of transfer; oriV, vegetative origin; trfA, replication initiator gene; Km$^r$, kanamycin resistance gene; $P_{maxF}$+op, methanol dehydrogenase combined with operator sequence from P. putida F1; gfp, green fluorescent protein encoding gene; estI, esterase encoding gene; and bgl, β-galactosidase encoding gene.

1b—Expression vectors and Induction profile of clones. To construct the inducible expression vectors, the operator sequence of the cmt operon from *P. putida* F1 was introduced downstream of a homogeneous promoter, $P_{mxaF}$. Plasmids, pCUM-gfp, pCUM-est, and pCUM-bgl, containing a GFP, esterase and β-galactosidase expression cassette, respectively, were constructed (FIG. 4.). *M. extorquens* (cymR2), transformed with these plasmids grew well for many generations under non-inducing conditions while still retaining their capacity for reproducible, high-level synthesis of reporter proteins when induced.

Figure 5:
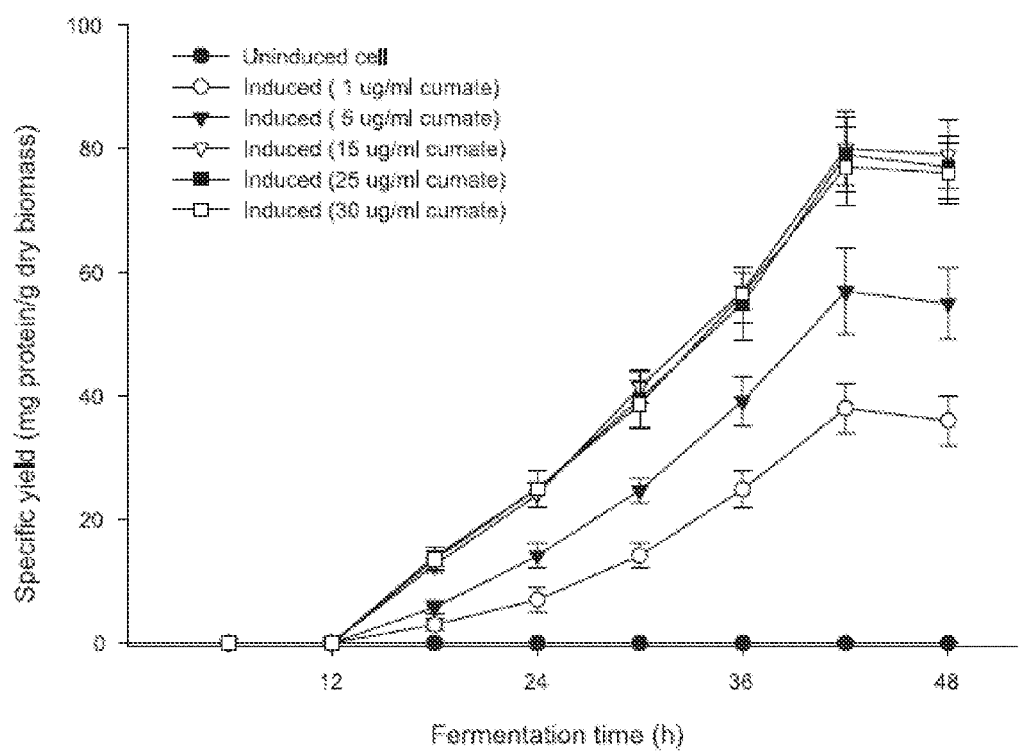
FIG. 5. Determination of cumate concentration required for optimal induction of recombinant gfp gene expression. The results indicate that the system is very finely controlled. The addition of 1 μg cumate/ml results in 47% induction of gene expression. The addition of 15-30 μg cumate/ml results in maximum gene expression.

To test the optimal concentration of inducer, cumate, recombinant *M. extorquens* (cymR2) transformed with pCUM-gfp was grown to mid-log phase (0.8-1.0 units at $OD_{600}$) at 30° C. followed by induction with cumate at different concentrations. Reporter gene expression was detectable 4 h post induction. Cumate induction was very sensitive since about 47% of reporter gene expression was obtained with 1 µg cumate/ml (FIG. 5). No growth difference was observed with the cumate concentrations tested (1-30 µg/ml), indicating that cumate does not negatively affect cell metabolism. Optimum cumate concentration for effective induction of reporter gene expression was 15 µg/ml (ca. 0.1 mM).

Figure 6:
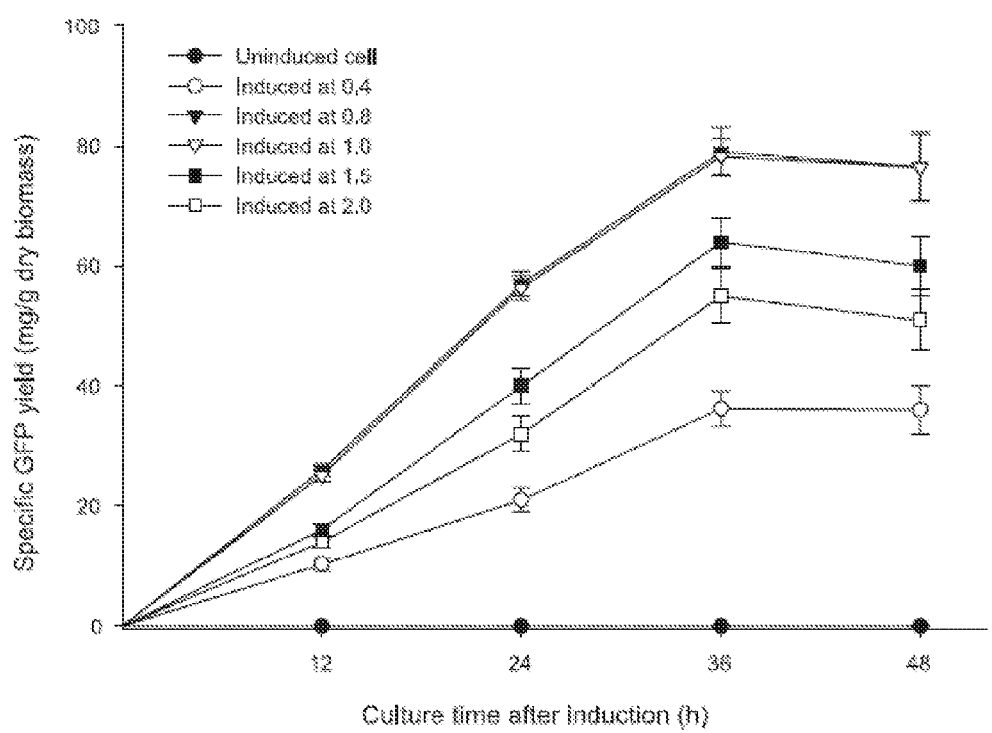
FIG. 6. Identification of the optimal time of induction. Maximum gene expression was obtained when the culture was induced with 15 μg cumate/ml at an $OD_{600}$ of 0.8-1.0. Induction at $OD_{600}$ of 0.4, 1.5, and 2.0 resulted in reduced expression of the target gene.

To determine the optimal induction point (time of induction), stably transformed *M. extorquens* cells were induced at different stages of batch growth ($OD_{600}$ of 0.4, 0.6, 0.8, 1.0, and 1.2) with 15 µg cumate/ml. Cells induced at $OD_{600}$ of 0.8-1.0 generated maximal protein yields in terms of specific activity, which accounts for 20-50% more protein production relative to the other induction points (FIG. 6).

To confirm induction profile of clones, three clones were selected from each selection plate of recombinant *M. extorquens* stably transformed with the following pCUM-derivatives, pCUM-GFP, pCUM-est, and pCUM-bgl. These clones were analyzed for induction profiles and basal expression levels. Clones cultured up to an $OD_{600}$ of 0.8-1.0 on CHOI medium containing kanamycin, did not produce detectable levels of recombinant proteins in the absence of cumate. When transformants were induced with cumate, expression of the recombinant protein was detected in all clones tested at 4 hours post induction. Production of GFP remained active even after 24 hours post induction with maximum expression at 30 hours post induction (FIG. 7a); recombinant protein expression was not detected in non-induced cells. Very similar results were obtained with pCUM-est and pCUM-bgl constructs (FIG. 7b,c).

Figure 7:
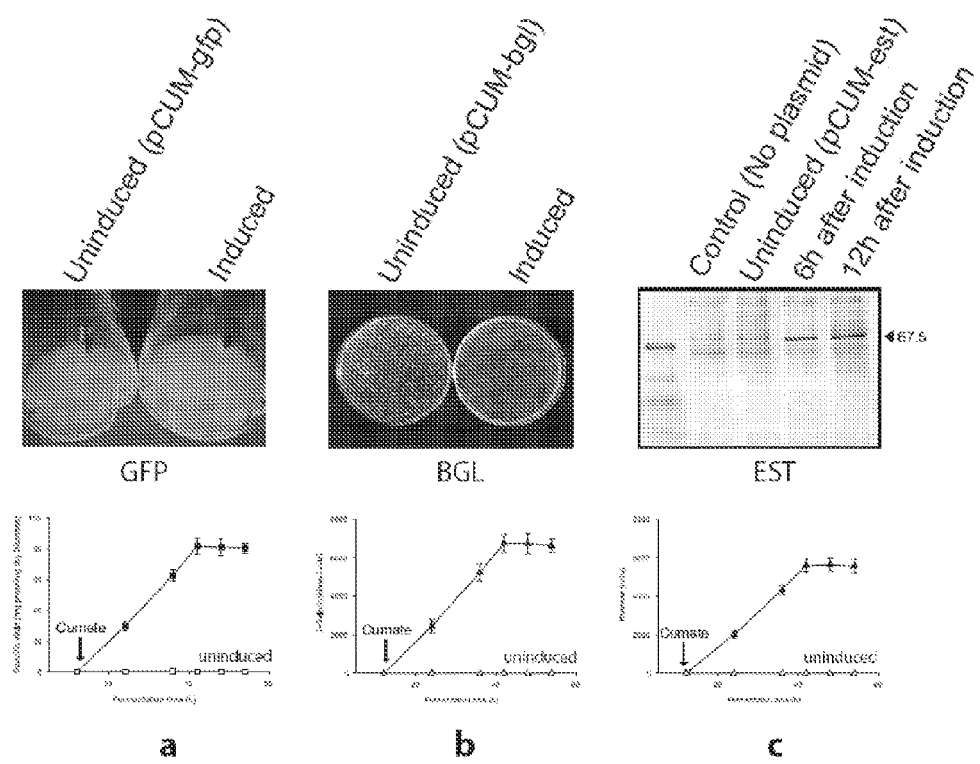
FIG. 7. Induction and production of recombinant proteins by the cumate-regulated expression system. The inducible expression system was validated with three different heterologous genes; Green Fluorescent Protein (A), β-galactosidase (B) and esterase (C). Without cumate induction, target proteins were not detected, as analyzed by UV for GFP, chromogenic substrate (x-gal) for β-galactosidase, and SDS-PAGE for esterase. Lower lane shows the recombinant protein production profiles from each construct. Arrow indicates the point of induction with cumate (15 μg/ml).

Using this system, recombinant protein yields in the range of 2-6 g/l were obtained under regulative conditions; more precisely, 6.1 g/l GFP (FIG. 7a), and 5,637±320 and 6,742±480 U of r esterase and β-galactosidase, respectively (FIG. 7b,c).

It is understood that the examples described above in no way serve to limit the true scope of this invention, but rather are presented for illustrative purposes.

REFERENCES

1. Kalyaeva, M. A., E. G. Ivanova, N. V. Doronina, N. S. Zakharchenko, Y. A. Trotsenko, and Y. I. Buryanov. 2003. The effect of aerobic methylotrophic bacteria on the in vitro morphogenesis of Soft Wheat (*Triticm aestivum*). Russian Journal of Plant Physiol. 50: 313-317.
2. Romanovskaya, V. A., S. M. Stolyar, Y. R. Malashenko, and T. N. Dodatko. 2001. The ways of plant colonization by *Methylobacterium* strains and properties of these bacteria. Microbiology, 70: 221-227.
3. Chistoserdova, L., S. W. Chen, A. Lapidus, and M. E. Lidstrom. 2003. Methylotrophy in *Methylobacterium extorquens* AM1 from a genomic point of view. J. Bacteriol. 185: 2980-2987.
4. Belanger, L., M. M. Figueira, D. Bourque, L. Morel, M. Beland, L. Laramee, D. Groleau, and C. B. Míguez. 2004. Production of heterologous protein by *Methylobacterium extorquens* in high cell density fermentation. FEMS Microbiol. Lett., 231: 197-204.
5. Fitzgerald, K. A. and M. E. Lidstrom. 2003. Overexpression of a heterologous protein, haloalkane dehalogenase, in a poly-β-hydroxybutyrate-deficient strain of the facultative methylotroph *Methylobacterium extorquens* AM1. Biotechnol. Bioeng. 81: 263-268.
6. Figueira, M. M., L. Laramee, J. C. Murrell, D. Groleau, and C. B. Míguez. 2000. Production of green fluorescent protein by the methylotrophic bacterium *Methylobacterium extorquens*. FEMS Microbiol. Lett. 193: 195-200.
7. Marx, C. J., B. N. O'Brien, J. Breezee, and M. E. Lidstrom. 2003. Novel methylotrophy genes of *Methylobacterium extorquens* AM1 identified by using transposon mutagenesis including a putative dihydromethanopterin reductase. J Bacteriol 185: 669-73.
8. Marx, C. J., and M. E. Lidstrom. 2004. Development of an insertional expression vector system for *Methylobacterium extorquens* AM1 and generation of null mutants lacking mtdA and/or fch. Microbiology 150: 9-19.
9. Anthony, C. 1993. Methanol dehydrogenase in Gram-negative bacteria. In: Davidson V (ed) Principles and applications of quinoproteins. Dekker, New York, pp 17-45.
10. Davidson, V. L. 1993. Methylamine dehydrogenase. In: Davidson V (ed) Principles and applications of quinoproteins. Dekker, New York, pp 73-85.
11. Trotsenko, Y. A., E. G. Ivanova, and N. V. Doronina. 2001. Aerobic methylotrophic bacteria as phytosymbionts. Microbiology 70: 623-632.
12. Bourque, D., B. Ouellette, G. Andre, and D. Groleau. 1992. Production of poly-β-hydroxybutyrate from methanol: characterization of a new isolate of *Methylobacterium extorquens*. Applied Microbiology and Biotechnology, 37: 7-12.
13. Bourque, D., Y. Pomerleau, and D. Groleau. 1995. High cell density production of poly-beta-hydroxybutyrate (PHB) from methanol by *Methylobacterium extorquens*: production of high-molecular-mass PHB. Appl. Microbiol. Biotechnol. 44: 367-376.
14. Van Dien, S. J., C. J. Marx, B. N. O'Brien, and M. E. Lidstrom. 2003. Genetic characterization of the carotenoid biosynthetic pathway in *Methylobacterium extorquens* AM1 and isolation of a colorless mutant. Appl Environ Microbiol. 69: 7563-6.
15. Doronina, N. V., E. G. Ivanova, and Y. A. Trotsenko. 2002. New evidence for the ability of methylobacteria and methanotrophs to synthesize auxins. Microbiology 71: 116-118.
16. Lidstrom, M. E. and L. Chistoserdova. 2002. Plants in the pink:Cytokinin production by *Methylobacterium*. J. Bacteriol. 184: 1818.
17. Choi, Y. J., C. B. Miguez, and B. H. Lee. 2004. Characterization and heterologous gene expression of a novel esterase from *Lactobacillus casei* CL96. Appl. Environ. Microbiol. 70: 3213-3221.
18. Gutierrez, J., D. Bourque, R. Criado, Y. J. Choi, L. M. Cintas, P. E. Hernandez, and C. B. Miguez. 2005. Heterologous extracellular production of enterocin P from *Enterococcus faecium* P13 in the methylotrophic bacterium *Methylobacterium extorquens*. FEMS Microbiol. Lett. 248: 125-131.
19. Fitzgerald, K. A. and M. E. Lidstrom. 2003. Overexpression of a heterologous protein, haloalkane dehalogenase, in a poly-β-hydroxybutyrate-deficient strain of the facultative methylotroph *Methylobacterium extorquens* AM1. Biotechnol. Bioeng. 81: 263-268.
20. Zhang M. and M. E. Lidstrom. 2003. Promoters and transcripts for genes involved in methanol oxidation in *Methylobacterium extorquens* AM1. Microbiol. 149: 1033-1040.
21. Eaton, R. W. 1996. p-Cumate catabolic pathway in *Pseudomonas putida* F1: cloning and characterization of DNA carrying the cmt operon. J. Bacteriol. 178: 1351-1362.
22. Eaton, R. W. 1997. p-Cymene catabolic pathway in *Pseudomonas putida* F1: cloning and characterization of DNA encoding conversion of p-cymene to p-cumate. J. Bacteriol. 179: 3171-3180.
23. Koch, B., L. E. Jensen, and O. Nybroe. 2001. A panel of Tn7-based vectors for insertion of the gfp marker gene or for delivery of cloned DNA into Gram-negative bacteria. J. Microbiol. Methods 45: 187-195.
24. Choi, Y. J., D. Bourque, L. Morel, D. Groleau, and C. B. Miguez. 2005. Multicopy-integration of heterologous genes and expression in the methylotroph *Methylobacterium extorquens* ATCC 55366. Appl. Environ. Microbiol. (submitted).
25. Marx, C. J. and M. E. Lidstrom. 2001. Development of improved versatile broad host-range vectors for use in methylotrophs and other Gram-negative bacteria. Microbiology, 147: 2065-2075.
26. Hung, M. N., Z. Xia, N. T. Hu, and B. H. Lee. 2001. Molecular and Biochemical Analysis of Two β-Galactosidases from *Bifidobacterium infantis* HL96. Appl. Environ. Microbiol. 67: 4256-4263.
27. Kademi A., L. Fakhreddine, N. Abdelkader, and J. C. Baratti. 1999. Effect of culture condition on growth and esterase production by the moderate thermophile *Bacillus circulars* MAS2. J. Ind. Microbiol. Biotech. 23: 188-193.
28. Sambrook, J. and D. W. Russel. 2000. Molecular Cloning. (third ed.), Cold Spring Harbor Laboratory, Cold Spring Harbor, N.Y.
29. Bradford, M. M. 1976. A rapid and sensitive method for the quantitation of microgram quantities of protein utilizing the principle of protein-dye binding. Anal. Biochem. 72: 248-254.

What is claimed is:

1. A methylotrophic or methanotrophic prokaryotic host cell comprising two copies, integrated into the chromosome of the host cell, of a polynucleotide sequence that encodes a cysteine metabolism repressor (cymR repressor) protein exhibiting repressor activity which is regulatable by addition of cumate, and further comprising a polynucleotide construct which comprises a constitutive promoter native to the host cell, wherein the promoter is fused to a cymR operator sequence which is operatively linked to at least one gene of interest, wherein a cymR repressor protein encoded by the polynucleotide sequence binds to the cymR operator sequence and wherein the addition of cumate upregulates expression of the at least one gene of interest.

2. A host cell as claimed in claim 1 which belongs to the genus *Methylobacterium*.

3. A host cell as claimed in claim 2 which belongs to the species *Methylobacterium extorquens*.

4. A host cell as claimed in claim 3 which belongs to the species identified as *Methylobacterium extorquens* ATCC55366.

5. A host cell as claimed in claim 1 wherein the cymR repressor protein is derived from *Pseudomonas putida*.

6. A host cell as claimed in claim 5 wherein the cymR operator sequence is at least a portion of the cmt operon of *Pseudomonas putida*.

7. A host cell as claimed in claim 1 wherein the promoter is $P_{mxaF}$.

8. A host cell as claimed in claim 1 wherein the at least one gene of interest comprises a gene that encodes a reporter protein.

9. A host cell as claimed in claim 8 wherein the reporter protein is selected from the group consisting of β-galactosidase, esterase and green fluorescence protein.

10. A host cell as claimed in claim 1 wherein the at least one gene of interest comprises a gene that encodes a recombinant protein.

11. A host cell as claimed in claim 1, wherein the two copies of the polynucleotide sequence that encodes the cymR repressor protein are inserted into the host cell chromosome at a mini-Tn7 transposon site.

12. A method for selectively controlling the expression of at least one gene of interest comprising the steps of a) obtaining a host cell as claimed in claim 1 wherein expression of the at least one gene of interest is repressed due to the repressor activity of the cymR repressor protein; b) culturing the host cell under conditions for expressing the cymR repressor protein; and c) exposing the host cell to cumate which inhibits the repressor activity and allows for expression of the at least one gene of interest.

* * * * *

SEQUENCE LISTING

<160> NUMBER OF SEQ ID NOS: 19

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gctgcagtca atcgtcaccc tttctcggtc                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gctgcagtca gcgatcggct cgttgccctg                                          30

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggctgcaggt tgacgacaac ggtgcgatg                                           29

<210> SEQ ID NO 4
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccgacgcgta tgtatatctc cttcttaaag                                          30

<210> SEQ ID NO 5
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gcttaagaag atggtgatca tgagtccaaa gagaagaac                                39

<210> SEQ ID NO 6
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6

-continued cagcggccgc ctagcgcttg aatttcgcgt accgctctcg cg  42

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
cagcggccgc gttgacgaca acggtgcgat gggtc  35

<210> SEQ ID NO 8
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cagggcccct agcgcttgaa tttcgcgtac cgctctcgcg  40

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
attagcttac gacgctacac cc  22

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
cacagcataa ctggactgat ttc  23

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
catcgcgatt gtcgattcgg  20

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ctgaaggaaa tcagctacat c  21

-continued

```
<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gctgcaggtc gactctagat cacctcctta agc                                    33

<210> SEQ ID NO 14
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cgaattcata atacaaacag accagattgt ctgtttgttg cccttaggat ccgcggtatc       60

<210> SEQ ID NO 15
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
cgctagcgaa catagagcgt tcaagtggc                                         29

<210> SEQ ID NO 16
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
catcgattta cagcttgacg acgagtacgc cg                                     32

<210> SEQ ID NO 17
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ggctagcgat caatctaaaa caaatc                                            26

<210> SEQ ID NO 18
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
catcgattta tttatttgta ataccgtctg c                                      31

<210> SEQ ID NO 19
```

```
<211> LENGTH: 26
<212> TYPE: DNA
<213> ORGANISM: Pseudomonas putida

<400> SEQUENCE: 19
acaaacagac cagattgtct gtttgt                                      26
```